United States Patent [19]

Miller, Jr. et al.

[11] Patent Number: 5,077,221

[45] Date of Patent: Dec. 31, 1991

[54] INDIRECT DETECTION THIN LAYER CHROMATOGRAPHY OF CATIONS

[75] Inventors: Theodore E. Miller, Jr., Midland, Mich.; Melanie C. Poon, Reynoldsburg, Ohio

[73] Assignee: The Dow Chemical Company, Midland, Mich.

[21] Appl. No.: 557,889

[22] Filed: Jul. 25, 1990

[51] Int. Cl.$^5$ .................. G01N 30/90; G01N 33/20
[52] U.S. Cl. ........................ 436/79; 210/658; 436/73; 436/162
[58] Field of Search .............. 436/73, 74, 79, 162, 436/169, 178; 210/658

[56] References Cited

U.S. PATENT DOCUMENTS 4,257,776  3/1981  Porter et al. .............. 436/162 X
4,414,842 11/1983  Small et al. ............... 73/61.1 C
4,744,952  5/1988  Ogita ...................... 436/162 X

OTHER PUBLICATIONS

Ma et al. Chemical Abstracts, vol. 108, Abstract No. 108:123532f, 1988.
Chromatography, *J. of Chromatography Library*, 22A, Edited by E. Heftmann, Elsevier Scientific Publ. Co., 1983.

*Primary Examiner*—Robert J. Hill, Jr.
*Attorney, Agent, or Firm*—Timothy S. Stevens

[57] ABSTRACT

A chemical analysis method for indirect detection thin layer chromatography of cations that provides a rapid indication of the amount and type of cation present with minimal equipment requirements. The method includes four steps. The first step is to equilibrate a thin layer cation exchange chromatography plate with a color-forming cation, such as with copper II, to form a prepared plate. The second step is to deposit a sample on the prepared plate to form a spotted plate, the sample containing a cation of interest, such as sodium I. The third step is to develop the spotted plate with a liquid solution containing the color-forming cation, such as a solution of copper II ions, to chromatograph the cation of the sample to form a developed plate. The last step is to expose the developed plate to a chemical agent, such as ammonia, to visualize the color-forming cation by a chemical reaction between the chemical agent and the color-forming cation to form a colored species, such as the blue colored copper II/ammonia complex. When this is done, the chromatographed sample cation is apparent as region of less intense color in a field of color on the plate generated by the colored species.

7 Claims, 1 Drawing Sheet

INDIRECT DETECTION THIN LAYER CHROMATOGRAPHY OF CATIONS

BACKGROUND OF THE INVENTION

Thin layer chromatography (TLC) is an important chemical analysis method. A thin layer of chromatographic stationary phase, such as silica gel granules and a binder or ion exchange resin granules and a binder, is coated on a suitable panel, such as a pane of glass or a sheet of plastic, to form a TLC plate. A sample is deposited near one edge of the plate and then this edge is immersed into a trough containing a developing solution. The developing solution advances up the TLC plate by capillary attraction in the layer of stationary phase. The components of the deposited sample are chromatographed into separate spots by the advancing developing solution in the layer of stationary phase. These spots are often not visible. Therefore, the TLC plate is usually then sprayed with a chemical that reacts with the components of the spots to form a colored species and thereby reveal the spots. The position of a spot on a TLC plate can be used to help identify the component of the sample responsible for the spot. The size of the spot and the intensity of its color can be used as an indication of the concentration of the component responsible for the spot. One of the primary benefits of the TLC method is that it can be used in situations where the cost and maintenance of complex instrumental methods of chemical analysis would be impractical.

The need for routine inorganic cation determinations is prevalent in several areas of chemical analysis such as water analysis and clinical diagnostics. Specifically, the quantitation of sodium I ($Na^+$), potassium I ($K^+$), magnesium II ($Mg^{+2}$) and calcium II ($Ca^{+2}$) is often required. Common methods for the determination of such cations includes flame photometry, ion selective electrodes, ion chromatography and indirect photometric chromatography.

Indirect photometric chromatography (IPC), as disclosed by Small and Miller in United States Pat. 4,414,842, was an important advance in the art of chromatography. One means of IPC of cations disclosed by Small and Miller was to inject a sample containing a cation of interest, such as sodium I, onto a cation exchange column and chromatograph it through the column with an eluent containing a dilute solution of copper II. The effluent from the column was then passed through a photometric detector set to detect the copper II but not the cation of interest. When the cation of interest passed from the column there was a transient decrease in the concentration of copper II which was seen by the detector as a negative chromatographic peak. It is known that copper II forms an intensely colored complex with ammonia and with diethyldithiocarbamate.

Although IPC is reliable and sensitive, it is not applicable in situations where the cost and maintenance of the required instrumentation is prohibitive. It would be an advance in the art of chemical analysis of cations if an indirect detection thin layer chromatography method could be developed for cations because thin layer chromatography is inherently a less complex method of analysis.

SUMMARY OF THE INVENTION

The present invention is a method for indirect detection thin layer chromatography of cations and includes four steps. The first step is to equilibrate a thin layer cation exchange chromatography plate with a color-forming cation to form a prepared plate. The second step is to deposit a sample on the prepared plate to form a spotted plate, the sample containing a cation of interest. The third step is to develop the spotted plate with a liquid solution containing the color-forming cation to chromatograph the cation of the sample to form a developed plate. The last step is to expose the developed plate to a chemical agent to visualize the color-forming cation by a chemical reaction between the chemical agent and the color-forming cation to form a colored species, the chromatographed sample cation being apparent as region of less intense color in a field of color on the plate generated by the colored species.

DETAILED DESCRIPTION OF THE INVENTION

The present invention uses the same general steps and equipment as are usually used in TLC. The primary difference is that the visualizing chemical agent does not cause the TLC spot to be colored but rather the field upon which this spot is located is colored by the visualizing chemical agent.

Figure 1:
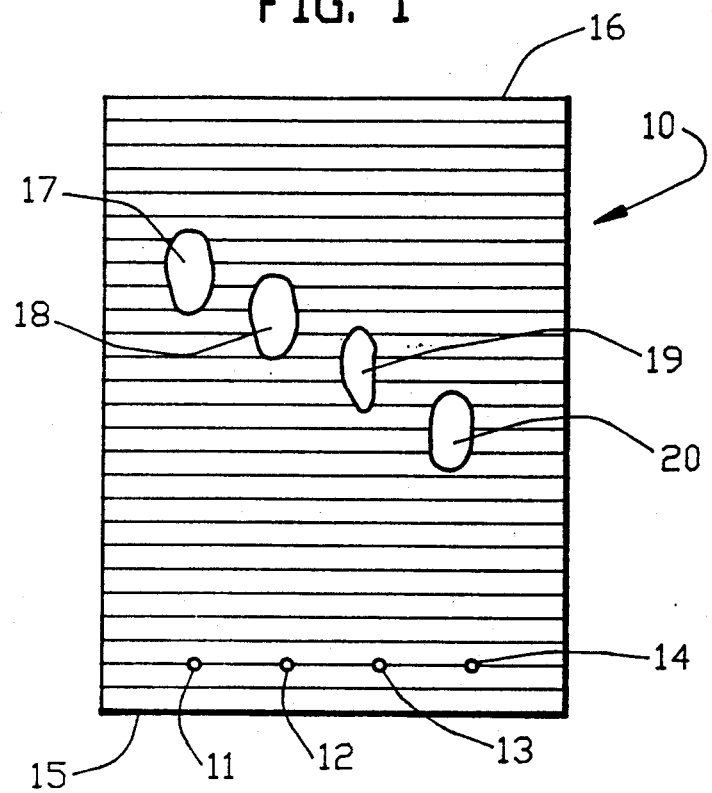
FIG. 1 is a drawing of a TLC plate exposed to ammonia according to the present invention to visualize various cations of interest as regions of less intense color in a field of blue color on the plate; and, FIG. 2 is a drawing of another TLC plate exposed to diethyldithiocarbamate according to the present invention to visualize various cations of interest as regions of less intense color in a field of yellow/gold color on the plate.

Referring now to FIG. 1, a Fixion 50X8 ion exchange TLC plate 10 (Chromatronix Corp., Mountain View, Calif.) is developed using a solution of 0.5 molar copper sulfate. The plate 10 is then dried. The plate 10 is then developed using a solution of 0.15 molar copper sulfate. The plate 10 is then dried. The plate 10 is now equilibrated with copper II, i.e., the cation exchange sites on the cation exchange TLC plate are at least partially in the $Cu^{+2}$ ion form. Copper II is an example of color-forming cation. A color-forming cation is a cation that forms an intensely colored species when it is reacted with a chemical agent to form a colored species. For example, copper II forms an intensely colored blue complex when it is reacted with the chemical agent ammonia. Copper II also forms an even more intensely colored yellow/gold species when it is reacted with diethyldithiocarbamate. The ion exchange TLC plate can also be equilibrated with the color-forming cation by simply immersing the plate into a solution of the color-forming cation. However, the Fixion 50X8 plate described above tended to blister and shed its ion exchange layer when so treated with the copper II solution. When possible, it is preferable to convert at least partially the ion exchanger of the ion exchange layer of the TLC plate to the color-forming cation form prior to coating the TLC plate with the so converted ion exchanger. The term "equilibrating a thin layer cation exchange chromatography plate with a color-forming cation to form a prepared plate" includes at least partially converting the cation exchanger of the cation exchange layer of the TLC plate to the color-forming cation form prior to coating the TLC plate with the so converted cation exchanger. The term "thin layer cation exchange chromatography plate" includes analytical and preparative TLC cation exchange chromatography plates as well as cation exchange papers for paper chromatography. The TLC plate 10 is now prepared to be spotted with a sample.

Twelve micrograms of sodium I from a three molar sample solution of sodium I is deposited on the plate 10 at spot 11. Twenty one micrograms of potassium I from a three molar sample solution of potassium I is deposited on the plate 10 at spot 12. Thirteen micrograms of magnesium II from a three molar sample solution of magnesium II is deposited on the plate 10 at spot 13. Twenty two micrograms of calcium II from a three molar sample solution of calcium II is deposited on the plate 10 at spot 14. The plate 10 is now a spotted plate.

The developing solution trough of a TLC developing chamber is filled with a 0.15 molar solution of copper chloride, i.e., 0.15 molar in copper II. The lower edge 15 of the plate 10 is immersed in this solution. Capillary attraction causes this solution to advance up the plate 10 toward the edge 16. When the front of this solution nears the edge 16, then the plate 10 is removed from the developing chamber. The plate 10 is now a developed plate.

The developing solution trough of a TLC developing chamber is filled with concentrated ammonium hydroxide solution. The developed plate is then placed in this chamber but is kept from direct contact with the ammonium hydroxide. However, the chamber contains ammonia gas from the ammonium hydroxide and the ammonia gas reacts with the copper II on the plate 10 to form a colored species, i.e., a blue colored copper ammonia complex which is apparent on the plate 10 as a field of blue color on the plate 10 indicated by the line shading of the plate 10. Above the spot 11 is a larger spot 17 of substantially less intense color. The spot 17 is due to the sodium I originally deposited at the spot 11. Above the spot 12 is a larger spot 18 of substantially less intense color. The spot 18 is due to the potassium I originally deposited at the spot 12. Above the spot 13 is a larger spot 19 of substantially less intense color. The spot 19 is due to the magnesium II originally deposited at the spot 13. Finally, above the spot 14 is a larger spot 20 of substantially less intense color. The spot 20 is due to the calcium II originally deposited at the spot 14.

In the above described method, it should be possible to substitute for the color-forming cation a cation that already is intensely colored, such as a cationic dye that is also a good ion exchange eluting ion. In this case the spots 17–20 would be apparent after the plate 10 is developed and it would be unnecessary to expose the plate 10 to ammonia or other such chemical agent to visualize the color-forming cation. If it is desired to chromatograph anions by this approach, then an anion exchange TLC plate should be similarly usable with an intensely colored anionic dye in the developing solution.

Figure 2:
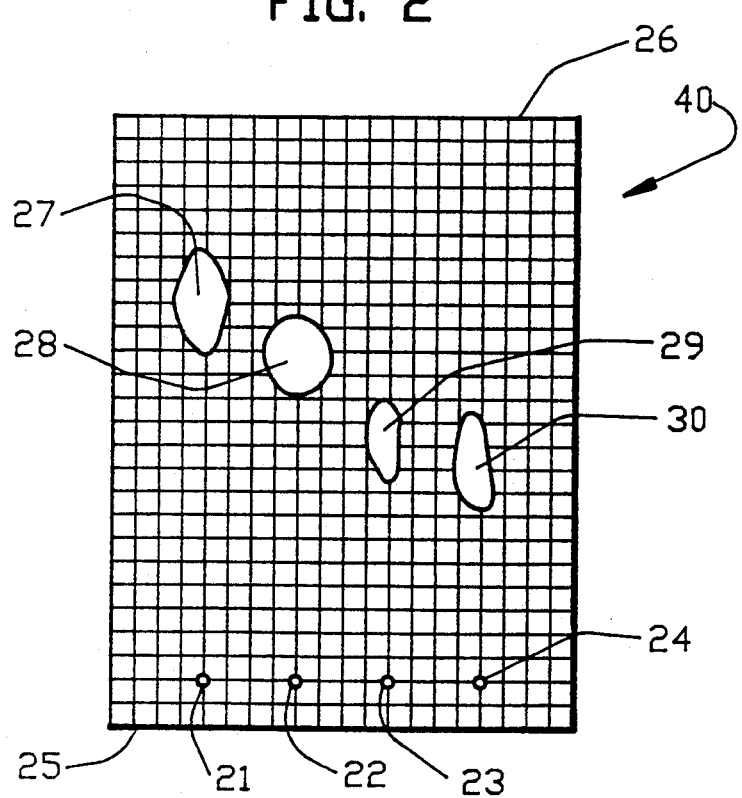

Referring now to FIG. 2, a Fixion 50X8 ion exchange TLC plate 40 (Chromatronix Corp., Mountain View, Calif.) is washed four times with a solution that is 0.12 molar in zinc II and 0.004 molar in copper II. The ion exchange layer of the plate 40 does not blister and fall off of the plate 40 as it does when the solution contains only copper II. The plate 40 is now equilibrated with copper II, i.e., the ion exchange sites on the ion exchange TLC plate are at least partially in the $Cu^{+2}$ ion form. Copper II is an example of a color-forming cation. A color-forming cation is a cation that forms an intensely colored species when it is reacted with a chemical agent to form a colored species. For example, copper II forms an intensely colored colored yellow/gold species when it is reacted with diethyldithiocarbamate. The TLC plate 40 is now prepared to be spotted with a sample.

Twelve micrograms of sodium I from a three molar sample solution of sodium I is deposited on the plate 40 at spot 21. Twenty one micrograms of potassium I from a three molar sample solution of potassium I is deposited on the plate 40 at spot 22. Thirteen micrograms of magnesium II from a three molar sample solution of magnesium II is deposited on the plate 40 at spot 23. Twenty two micrograms of calcium II from a three molar sample solution of calcium II is deposited on the plate 40 at spot 24. The plate 40 is now a spotted plate.

The developing solution trough of a TLC developing chamber is filled with a solution that is 0.12 molar in zinc II and 0.004 molar in copper II. The lower edge 25 of the plate 40 is immersed in this solution. Capillary attraction causes this solution to advance up the plate 40 toward the edge 26. When the front of this solution nears the edge 26, then the plate 40 is removed from the developing chamber. The plate 40 is now a developed plate.

The plate 40 is immersed in a dilute aqueous solution of diethyldithiocarbamate. The diethyldithiocarbamate reacts with the copper II on the plate 40 to form a colored species, i.e., a yellow/gold colored species which is apparent on the plate 40 as a field of yellow/gold color on the plate 40 indicated by the crosshatch shading of the plate 40. Above the spot 21 is a larger spot 27 of substantially less intense color. The spot 27 is due to the sodium I originally deposited at the spot 21. Above the spot 22 is a larger spot 28 of substantially less intense color. The spot 28 is due to the potassium I originally deposited at the spot 22. Above the spot 23 is a larger spot 29 of substantially less intense color. The spot 29 is due to the magnesium II originally deposited at the spot 23. Finally, above the spot 24 is a larger spot 30 of substantially less intense color. The spot 30 is due to the calcium II originally deposited at the spot 24.

The sample of the present invention can contain a single cation of interest or a plurality of cations of interest and still be within the broad scope of the claims. Generally, the position of a spot on the TLC plate is indicative of the identification of the cation responsible for the spot. The size of the spot and the degree of its reduction in color relative to the field is indicative of the concentration of the cation responsible for the spot. Just as in regular TLC, in the present invention a densitometer can be used to instrumentally measure a spot.

What is claimed is:

1. A method for indirect detection thin layer chromatography of cations, comprising the steps of:
    (a) equilibrating a thin layer cation exchange chromatography plate with a color-forming cation to form a prepared plate;
    (b) depositing a sample on the prepared plate to form a spotted plate, the sample containing a cation of interest;
    (c) developing the spotted plate with a liquid solution containing the color-forming cation to chromatograph the cation of the sample to form a developed plate; and
    (d) exposing the developed plate to a chemical agent to visualize the color-forming cation by a chemical reaction between the chemical agent and the color-forming cation to form a colored species, the chromatographed sample cation being apparent as region of less intense color in a field of color on the plate generated by the colored species.

2. The method of claim 1, wherein the color-forming cation is copper II and the chemical agent is ammonia.

3. The method of claim 2, wherein the cation of interest is selected from the group consisting of sodium I, potassium I, calcium II and magnesium II.

4. The method of claim 1, wherein the color-forming cation is copper II and the chemical agent is diethyldithiocarbamate.

5. The method of claim 4, wherein the cation of interest is selected from the group consisting of sodium I, potassium I, calcium II and magnesium II.

6. The method of claim 1, wherein the liquid solution contains zinc II and copper II and the chemical agent is diethyldithiocarbamate.

7. The method of claim 6, wherein the cation of interest is selected from the group consisting of sodium I, potassium I, calcium II and magnesium II.

* * * * *